United States Patent [19]
Yamada et al.

[11] Patent Number: 5,695,625
[45] Date of Patent: Dec. 9, 1997

[54] OXYGEN CONCENTRATION DETECTOR

[75] Inventors: Masaru Yamada, Tokoname; Masayuki Hiroshima, Anjo, both of Japan

[73] Assignee: Nippondenso Co., Ltd., Kariya, Japan

[21] Appl. No.: 597,915

[22] Filed: Feb. 7, 1996

[30] Foreign Application Priority Data

Feb. 8, 1995 [JP] Japan .................. 7-044943

[51] Int. Cl.$^6$ .................................. G01N 27/407
[52] U.S. Cl. ............... 204/427; 204/426; 204/428; 205/784.5
[58] Field of Search ................... 204/421–429

[56] References Cited

U.S. PATENT DOCUMENTS

| | | | |
|---|---|---|---|
| 4,159,234 | 6/1979 | Zifler et al. | 204/428 |
| 4,347,113 | 8/1982 | Fischer et al. | 204/428 |
| 4,450,065 | 5/1984 | Yamada et al. | 204/426 |
| 4,718,999 | 1/1988 | Suzuki et al. | 204/426 |
| 4,824,528 | 4/1989 | Polak et al. | 204/426 |
| 4,859,307 | 8/1989 | Nishizawa et al. | 204/426 |
| 4,883,947 | 11/1989 | Murase et al. | |
| 4,980,044 | 12/1990 | Ker . | |
| 5,164,068 | 11/1992 | Udo et al. | 204/426 |
| 5,238,551 | 8/1993 | Katsu et al. | 204/427 |

FOREIGN PATENT DOCUMENTS

| | | |
|---|---|---|
| 64-32162 | 2/1989 | Japan . |
| 2-251745 | 10/1990 | Japan . |
| 3-277958 | 12/1991 | Japan . |
| 5-126789 | 5/1993 | Japan . |

*Primary Examiner*—T. Tung
*Attorney, Agent, or Firm*—Cushman, Darby & Cushman IP Group of Pillsbury Madison & Sutro LLP

[57] ABSTRACT

According to the present invention, an oxygen concentration detector includes a housing, a detecting element inserted into said housing and a cover for covering a top portion of said detecting element. The detecting element is made of solid electrolyte and includes an atmospheric chamber therein. The cover includes an air vent portion for introducing air into said atmospheric chamber of the detecting element. The detecting element includes an air introducing path open to the atmospheric chamber at a side wall of the detecting element. It is possible to provide an oxygen concentration detector capable of introducing the air into the atmospheric chamber and maintaining an oxygen concentration in the atmospheric chamber at the same level as an atmosphere constantly.

15 Claims, 14 Drawing Sheets

ОXYGEN CONCENTRATION DETECTOR

CROSS REFERENCE TO RELATED APPLICATION

This application is based on and claims priority of Japanese Patent Application No. 7-44943 filed on Feb. 8, 1995, the content of which is incorporated herein by reference.

BACKGROUND OF THE INVENTION

1. Field of the Invention

The present invention relates to an oxygen concentration detector used for an air fuel ratio control or the like in an automotive engine.

2. Description of Related Art

Conventionally, an oxygen concentration detector includes a housing, a detecting element disposed inside the housing, and a cover covering a top portion of the detecting element at a top portion of the housing. The detecting element has an atmospheric chamber therein and is made of a solid electrolyte. An air vent portion for introducing air to the atmospheric chamber of the detecting element is provided at the cover.

As illustrated in FIG. 18, a detecting element 9 is structured by laminating a plate-shaped solid electrolyte 951 and ceramic plates 952 and 953 one another.

A slit is provided at the ceramic plate 952 to form an atmospheric chamber 900 after being laminated. An opening end portion of the slit is a top end opening portion 90 for ventilating the atmospheric chamber in the detecting element 9.

A connecting piece 221 and lead portions 222 and 223 conducting electrically to an outside electrode 22 are provided in the solid electrolyte 951. Further, an inside electrode is provided at a portion facing the slit at the solid electrolyte 951. A lead portion 233 conducts electrically to the inside electrode.

A heating portion 241 and a lead portion 242 electrically conducting to the heating portion 241 are provided on the ceramic plate 953.

In the oxygen concentration detector, an air 89 flowing from the air vent portion flows into the atmospheric chamber 900 from the top end opening portion 90 of the detecting element 9 through air inlet openings (not shown) of the oxygen concentration detector. In this way, when detecting the oxygen concentration, oxygen flows in a measured gas chamber through the solid electrolyte 951 from the atmospheric chamber 900. Thus, when the atmospheric chamber is deficient in oxygen, the oxygen can be supplied to the atmospheric chamber 900.

However, in the oxygen concentration detector having the detecting element 9, that the atmospheric chamber 900 is deficient in oxygen may not be overcome.

That is, as illustrated in FIG. 19, the detecting element 9 is narrow and long and a bottom portion of the atmospheric chamber 900 is apart from the top end opening portion 90 and an opening area of the top end opening portion 90 is small.

Thus, as illustrated in FIG. 19, an air 81 flowing from the top end opening portion 90 is circulated at a top portion of the atmospheric chamber 900 and may flow out from the atmospheric chamber 900. On the other hand, the air 89, in an oxygen deficiency state, existing inside the atmospheric chamber 900 is circulated and stays around the bottom portion of the atmospheric chamber 900. In this case, oxygen concentration inside the atmospheric chamber 900 cannot be maintained at the same level as an atmosphere, and therefore, detection accuracy of the oxygen concentration detector is deteriorated in accordance with the deficiency of oxygen.

When the oxygen concentration detector is used as an air fuel ratio sensor used for the air fuel ratio control of the automotive engine, the following problem may be caused.

That is, when the air fuel ratio is in a rich state, a large amount of oxygen in the atmospheric chamber flows to the measured gas chamber through the solid electrolyte. As described above, the detecting element 9 is structured not to be able to introduce a large amount of the air to the atmospheric chamber efficiently.

Therefore, as illustrated in FIG. 20, when a voltage-current characteristic of the detecting element is in a rich state, a flat characteristic can not be obtained. Thus, purifying performance of exhaust gas in the rich state is deteriorated.

This kind of problem is easily caused when a vehicle travels with a high speed and on continuous ascending hills.

SUMMARY OF THE INVENTION

In view of the foregoing problems, it is a primary object of the present invention to provide an oxygen concentration detector capable of introducing air to an atmospheric chamber is easy and maintaining the oxygen concentration in the atmospheric chamber at the same level as an atmosphere.

A remarkable feature of the present invention is that the detecting element has the air introducing path open to the atmospheric chamber on a side wall of the detecting element.

The air introducing path is set to a length in which the measured gas in the measured gas chamber does not enter the atmospheric chamber. That is, in the oxygen concentration detector, a seal material is generally provided between the detecting element and the housing so that air is not mixed between the atmospheric chamber and the measured gas chamber. In this case, a bottom end of the air introducing path is above the seal material.

The air introducing path is, for example, a long hole in the axial direction of the detecting element or at least a hole. The long hole is a U-shaped long hole having a top end opening portion at a top end of the detecting element.

It is preferable that the detecting element has an inclined surface in the axial direction of the detecting element and the long hole is provided at the inclined surface. That is, the detecting element has the inclined surface, in the axial direction, extending from the top end opening to a side wall of the detecting element. The long hole is provided on the inclined surface and the long opening hole to form the air introducing path. In this case, since an overall inclined surface is the air introducing path, the air can flow more easily.

The present invention can be applied to the test tube type detecting element and the laminated type detecting element.

In the oxygen concentration detector according to the present invention, an air introducing path is provided at a side wall of the detecting element, and air is introduced into the atmospheric chamber through the top end opening portion of the detecting element and the air introducing path.

The air introducing path is provided at the side wall of the detecting element. Therefore, a fresh air flowing from the air introducing path is introduced into the bottom portion of the atmospheric chamber easily and circulates so as to mix an entire inside of the atmospheric chamber.

In this way, oxygen can be easily supplied to the atmospheric chamber in the oxygen deficient state.

Further, the air flows into the atmospheric chamber from both the top end opening portion and the air introducing path. Thus, a large amount of air can flow in the atmospheric chamber at a time.

According to the present invention, it is possible to provide an oxygen concentration detector capable of introducing the air into the atmospheric chamber and maintaining an oxygen concentration in the atmospheric chamber at the same level as an atmosphere.

BRIEF DESCRIPTION OF THE DRAWINGS

Additional objects and advantages of the present invention will be more readily apparent from the following detailed description of preferred embodiments thereof when taken together with the accompanying drawings in which.

DETAILED DESCRIPTION OF THE PRESENTLY PREFERRED EMBODIMENTS

The preferred embodiments of the present invention are hereinafter described with reference to the accompanying drawings.

An oxygen concentration detector according to an embodiment of the present invention is described with reference to FIGS. 1 through 7.

Figure 1:
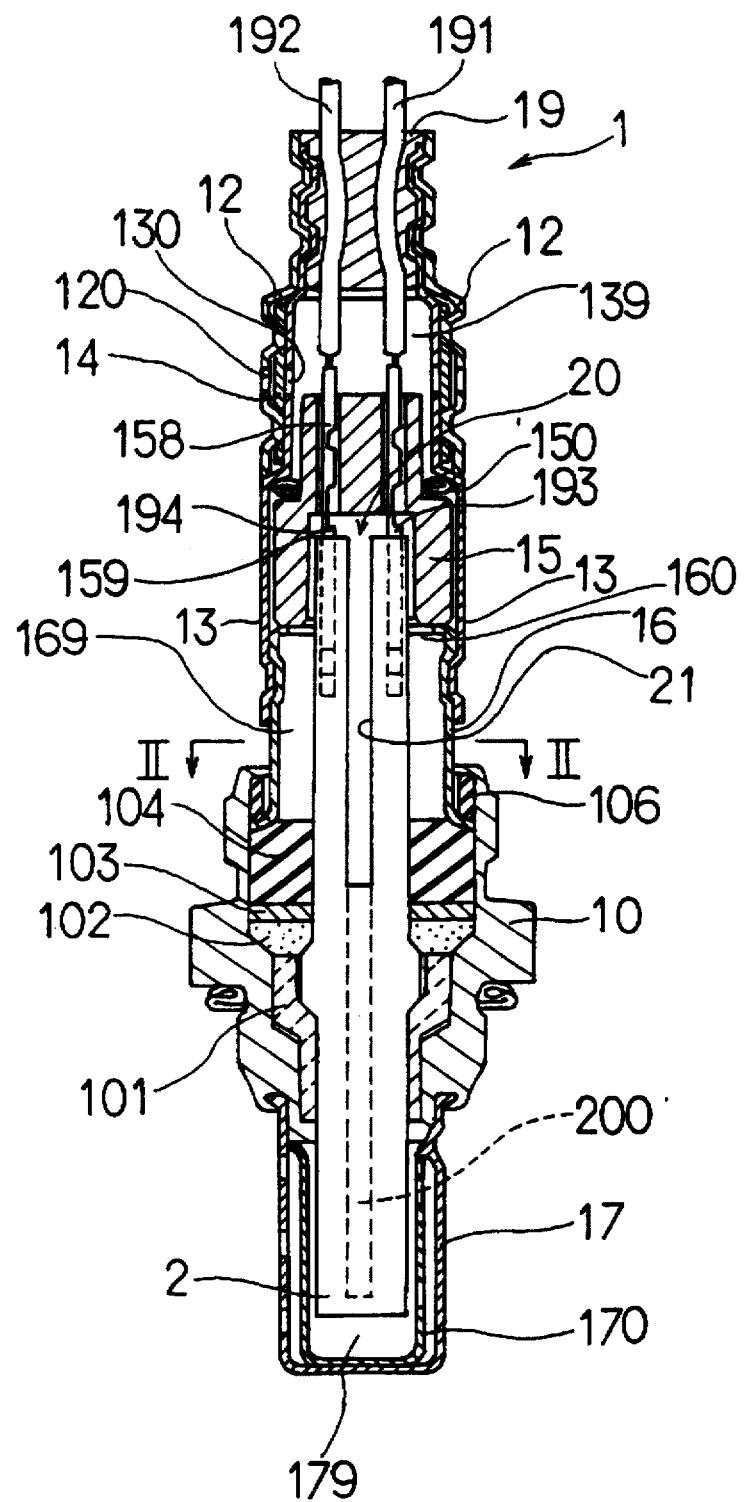
FIG. 1 is a cross sectional view illustrating an oxygen concentration detector according to an embodiment of the present invention.

As illustrated in FIG. 1, an oxygen concentration detector 1 of the present invention includes a housing 10, a detecting element 2 inserted into the housing 10, and covers 12, 13 and 16 provided at a top portion of the housing 10 and covering a top portion of the detecting element 2. The detecting element has an atmospheric chamber 200 therein and is made of a solid electrolyte 251 as shown in FIG. 2.

Air vent portions 120 and 130 are provided on the covers 12 and 13 to introduce the air into the atmospheric chamber 200 of the detecting element 2.

Figure 2:
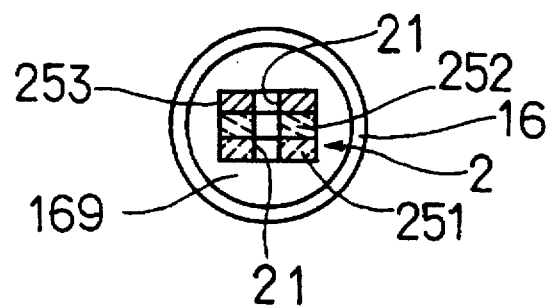
FIG. 2 is a perspective view taken along line II—II in FIG. 1.
Figure 3:
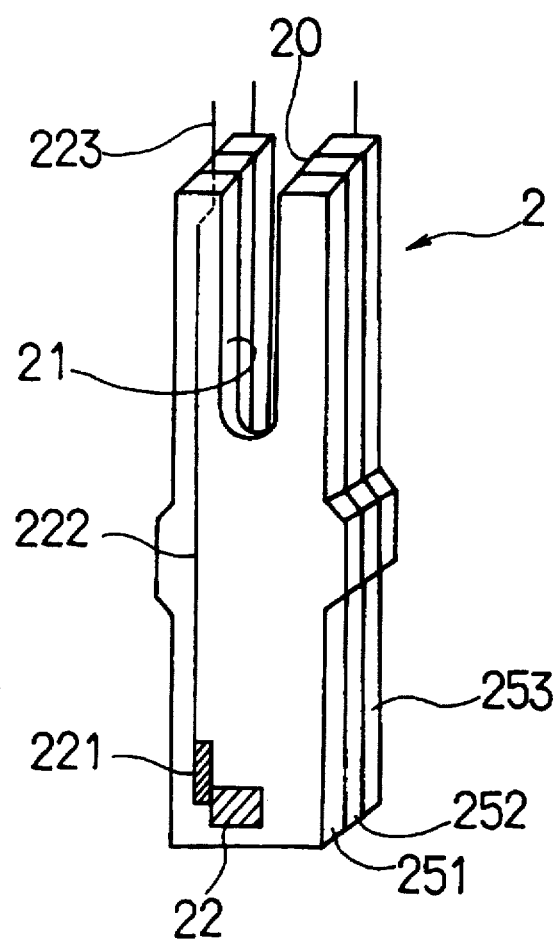
FIG. 3 is a perspective view illustrating a detecting element according to the embodiment.

As illustrated in FIGS. 2 and 3, the detecting element 2 has, at a side wall, an air introducing path 21 having a long hole open to the atmospheric chamber 200.

As illustrated in FIG. 1, the detecting element 2 is inserted into the housing 10 with an insulator 101 therebetween in the oxygen concentration detector 1. The detecting element 2 has a flange portion at a side portion thereof and is in contact with the insulator 101 below the flange portion.

A powdery seal material 102 is filled on the flange portion so as to be pressurized by a pad 103 and an insulator 104.

The cover 16 is disposed in such a manner that a bottom end of the cover 16 is in contact with a top end of the insulator and is fixed firmly to the housing 10 by crimping with a metallic ring 106 therebetween. As illustrated in FIGS. 1 and 2, a space portion 169 is formed by the cover 16 at a side portion of the air introducing path 21 in the detecting element 2.

Next, the cover 13 is installed on the cover 16 to cover the top end of the cover 16. An air vent portion 130 is provided at a top portion of the cover 13 and a pipe-shaped water repellent filter 14 is disposed to cover the air vent portion 130.

The filter cover 12 is disposed outside of the water repellent filter 14 to fix the water repellent filter 14 to the cover 13. The air vent portion 120 is provided at the filter cover 12 at the same position as the cover 13. The air vent portions 120 and 130 are through holes provided at the filter covers 12 and 13. A space portion 139 is surrounded by an insulator 15 and a bush 19.

Further, the insulator 15 is disposed at the top end of the cover 16 to cover a top end of the detecting element 2. A cover portion 159 for covering the top end of the detecting element 2 and an inserting portion 158 for inserting a lead terminals 193 and 194 connected to the detecting element 2 are provided at the insulator 15. A wave washer 150 is disposed between the cover 13 and the insulator 15.

Double laminated protecting covers 17 and 170 are provided below the housing 10 to cover a bottom portion of the detecting element 2, and a measured gas chamber 179 is thereby formed.

In FIG. 1, the bush 19 fixes the lead wires 191 and 192 for taking out an output of the detecting element 2.

Figure 4:
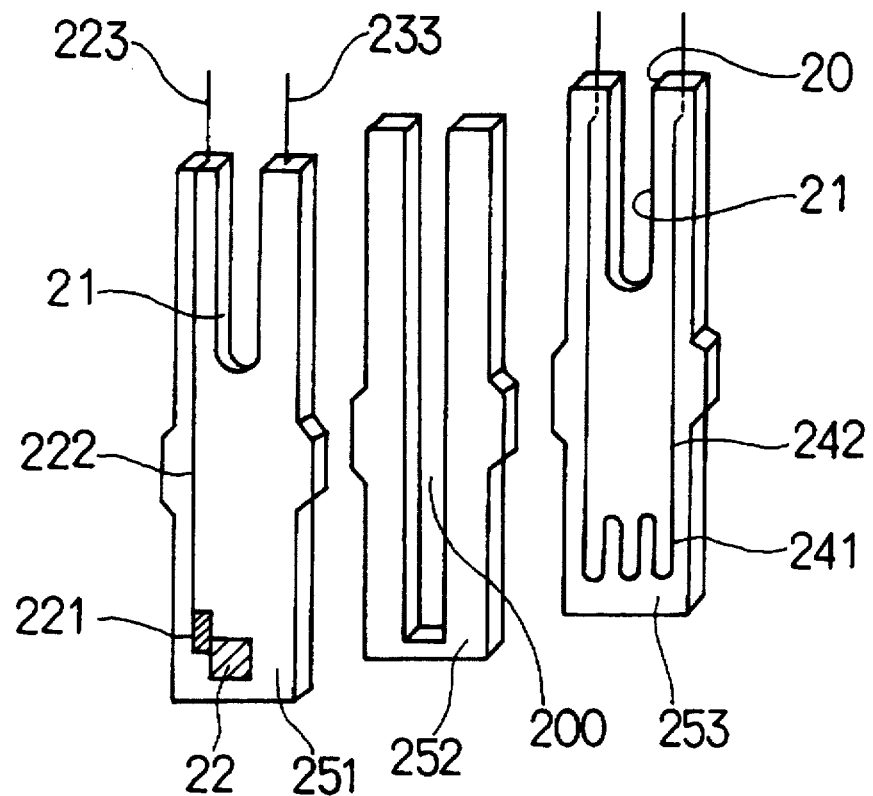
FIG. 4 is an exploded view illustrating the detecting element according to the embodiment.
Figure 5:
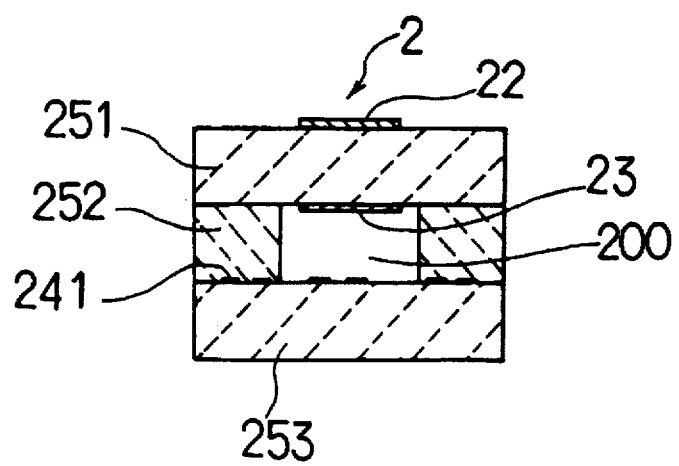
FIG. 5 is a transverse cross-sectional view illustrating the detecting element according to the embodiment.

As illustrated in FIGS. 3 through 5, the detecting element 2 is structured by laminating the solid electrolyte 251 and ceramic plates 252 and 253 one another.

The solid electrolyte 251 includes a slit, the outside electrode 22 is provided on a front surface of the solid electrolyte 251, and the inside electrode 23 is provided on a surface opposing to the outside electrode 22.

The connecting piece 221 and lead portions 222 and 223 for connecting the outside electrode 22 to the lead terminal 104 are provided at the solid electrolyte 251. The outside electrode 22 is provided in such a manner that the outside electrode 22 faces the measured gas chamber 179 in the oxygen concentration detector 1. The inside electrode 23 is provided to face the atmospheric chamber 200. A lead portion 133 is extended from the inside electrode 23.

The ceramic plate 253 includes a slit, and a heating portion 241 and a lead portion 242 electrically conducting to the heating portion 241 are provided on the ceramic plate 253.

Next, a slit, which is longer than the slit at the solid electrolyte 251 and the ceramic plate 253, is provided on the ceramic plate 252.

Further, the slit provided on the solid electrolyte 251 and the ceramic plate 253 forms an air introducing path 21 after the detecting element 2 are assembled by laminating the solid electrolyte 251, the ceramic plates 251 and 252. The slit provided on the ceramic plate 252 forms the atmospheric chamber 200. An opening end portion of the slit is a top end opening portion 20 of the detecting element 2.

Next, an operation and effect of the present embodiment is described below.

Figure 6:
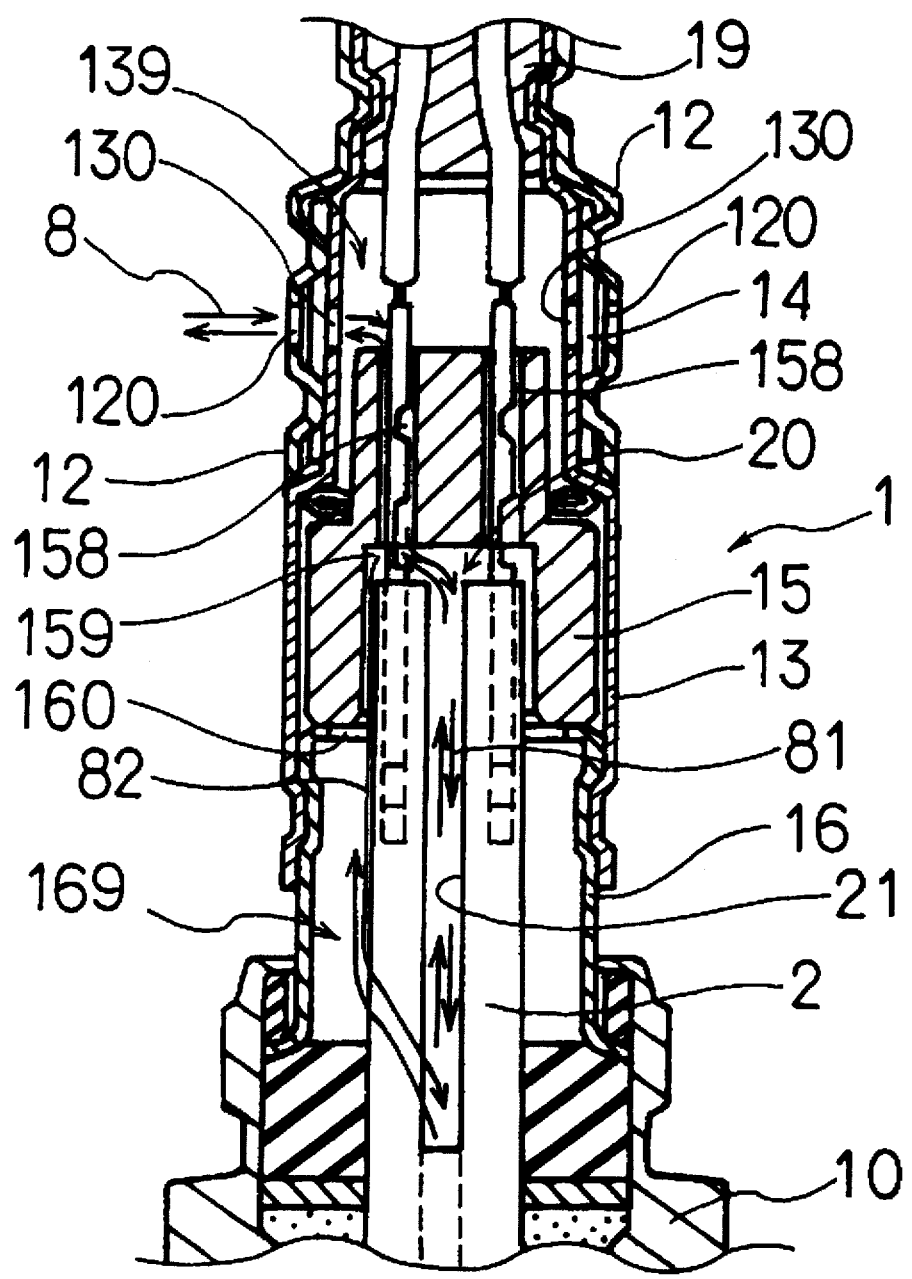
FIG. 6 is an explanatory view illustrating air flow inside the oxygen concentration detector according to the embodiment.
Figure 7:
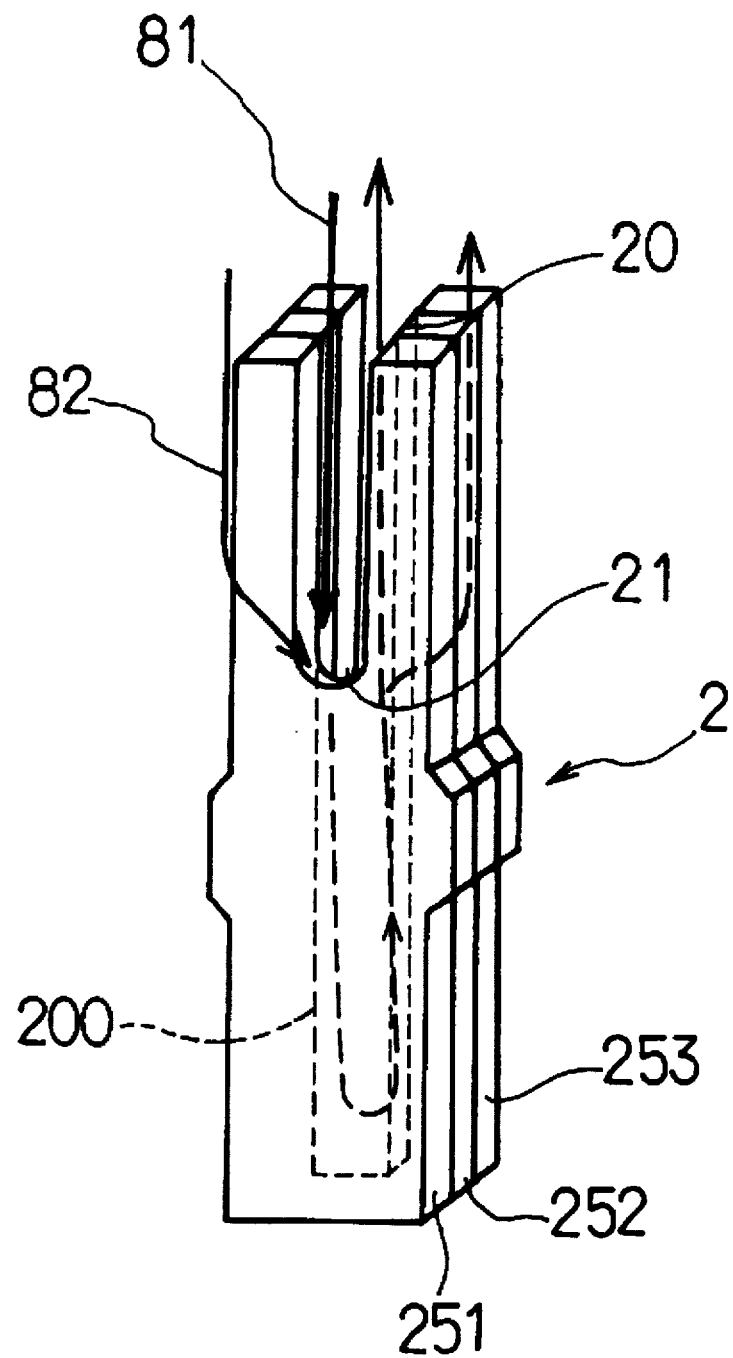
FIG. 7 is an explanatory view illustrating the air flow inside the detecting element according to the embodiment.

As illustrated in FIGS. 6 and 7, in the oxygen concentration detector 1, an air 8 is introduced from the air vent portion 120 provided at the filter cover 12. The air 8 is introduced to the space portion 139 through the porous water repellent filter 14 and the air vent portion 130.

Next, the air 8 flows in the covering portion 159 through the inserting portion 158 provided at the insulator 15. The air 8 is separated into an air 81 and an air 82.

The air 81 flows in the atmospheric chamber 200 from the top end opening portion 20 of the detecting element 2.

Air 82 flows from opening hole portion 160 of cover 16 through space portion 169, through air introducing path 21 into atmospheric chamber 200. As illustrated in FIG. 7, the air 81 and the air 82 are merged inside the detecting element and circulate so as to mix the entire atmospheric chamber 200. By this circulation, the air in the atmospheric chamber 200 in the oxygen deficient state flows out from the atmospheric chamber 200. The air in the atmospheric chamber 200 is released to the outside of the oxygen concentration detector 1 by flowing back to the above-described circulation.

Therefore, the air in the atmospheric chamber 200, which oxygen concentration is reduced, is replaced with a fresh air introduced from an atmosphere.

In the oxygen concentration detector of this embodiment, a large amount of the air can flow in the atmospheric chamber 200 at a time from the top end opening portion 20 and the air introducing path 21. Thus, oxygen concentration in the measured gas can be measured accurately.

According to this embodiment, the oxygen concentration detector capable of introducing the air to the atmospheric chamber easily and maintaining the atmospheric chamber at the same level as the atmosphere can be provided.

Modifications of the above embodiment is described with reference to FIGS. 8 through 11.

FIGS. 8 through 11 illustrate the detecting element having various kinds of air introducing paths.

Figure 8:
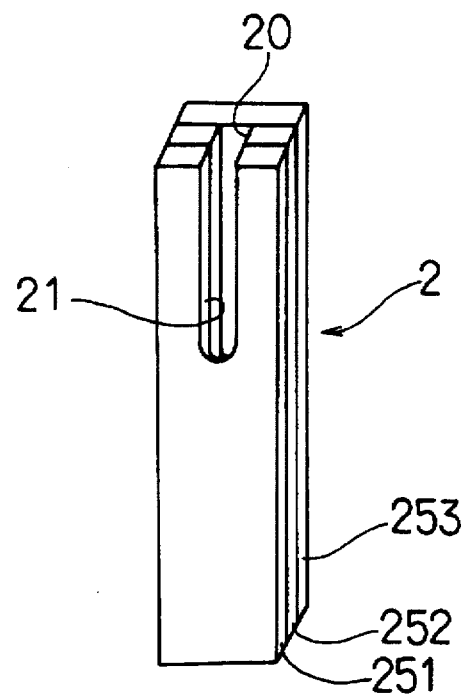
FIG. 8 is a perspective view illustrating the detecting element according to a modification of the embodiment of the present invention.

In FIG. 8, in the detecting element 2, the air introducing path 21 having the long hole is provided only on one side of the detecting element 2 (one of the ceramic plate 252 and the solid electrolyte 251).

Figure 9:
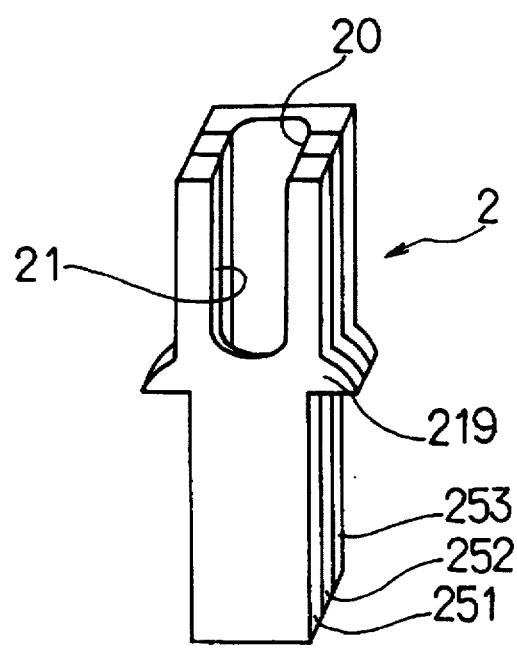
FIG. 9 is a perspective view illustrating a detecting element according to another modification of the embodiment.

In FIG. 9, the detecting element 2 includes flange portions 219 and the air introducing path 21 having the long hole provided only on one side of the detecting element 2 (one of the ceramic plate 252 and the solid electrolyte 251).

Figure 10:
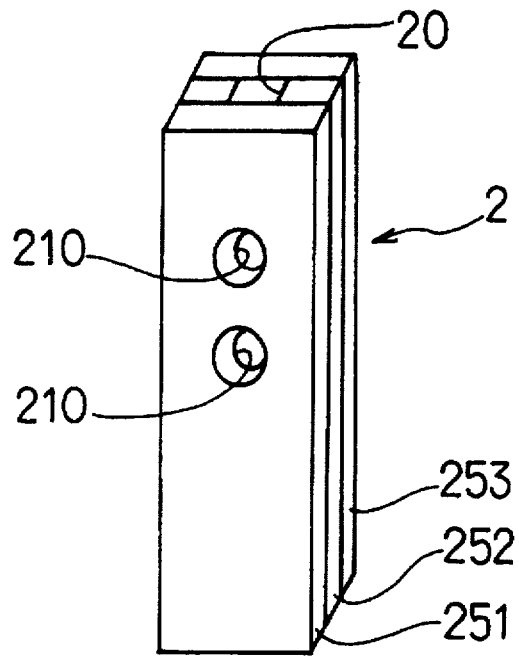
FIG. 10 is a perspective view illustrating a detecting element according to further another modification of the embodiment.

In FIG. 10, in the detecting element 2, two through holes are provided on the solid electrolyte 251 as the air introducing path 210.

Figure 11:
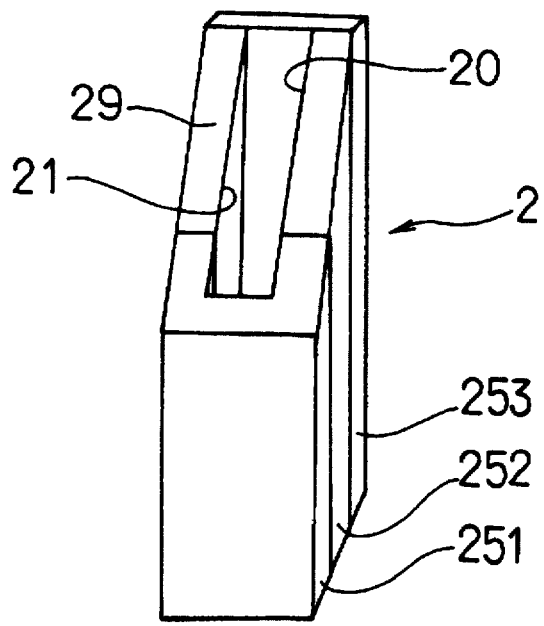
FIG. 11 is a perspective view illustrating a detecting element according to still another modification of the embodiment.

In FIG. 11, the detecting element 2 includes an inclined surface 29 extending from the top end opening portion 20 to a side surface of the detecting element 20 along the axial direction and a long hole at the inclined surface 29 as the air introducing path 21. In each case, the top end opening portion 20 is provided at a center portion of the detecting element 2 in the same manner as the conventional type. The other parts are the same as the first embodiment.

Next, in the oxygen concentration detector with the detecting element, in FIG. 8, as a portion forming the air introducing path 21 is defined by one side surface (side wall), strength of the detecting element 2 can be maintained. In FIG. 9, while maintaining the detecting element 2 in a predetermined position by flange portions 219, a cross-sectional area of the air introducing path 21 can be enlarged.

In FIG. 10, as the air introducing path 21 can be formed easily only by a hole opening process on the detecting element 2, the number of processing can be reduced. Further, the strength of the detecting element 2 can be maintained. In FIG. 11, a sharp edge portion at the top end opening portion 20 of the detecting element 2 is altered, so that cracking or breaking of the detecting element 2 can be prevented.

Although the oxygen concentration detector using the laminated type detecting element is described in the first and second embodiments, in another embodiment illustrated in FIGS. 12 through 17, the oxygen concentration detector 1 includes a cup-shaped detecting element 3. The cup-shaped detecting element 3 is formed in generally a test tube shape, and a separate heater 18 is inserted into the atmospheric chamber 300.

Figure 12:
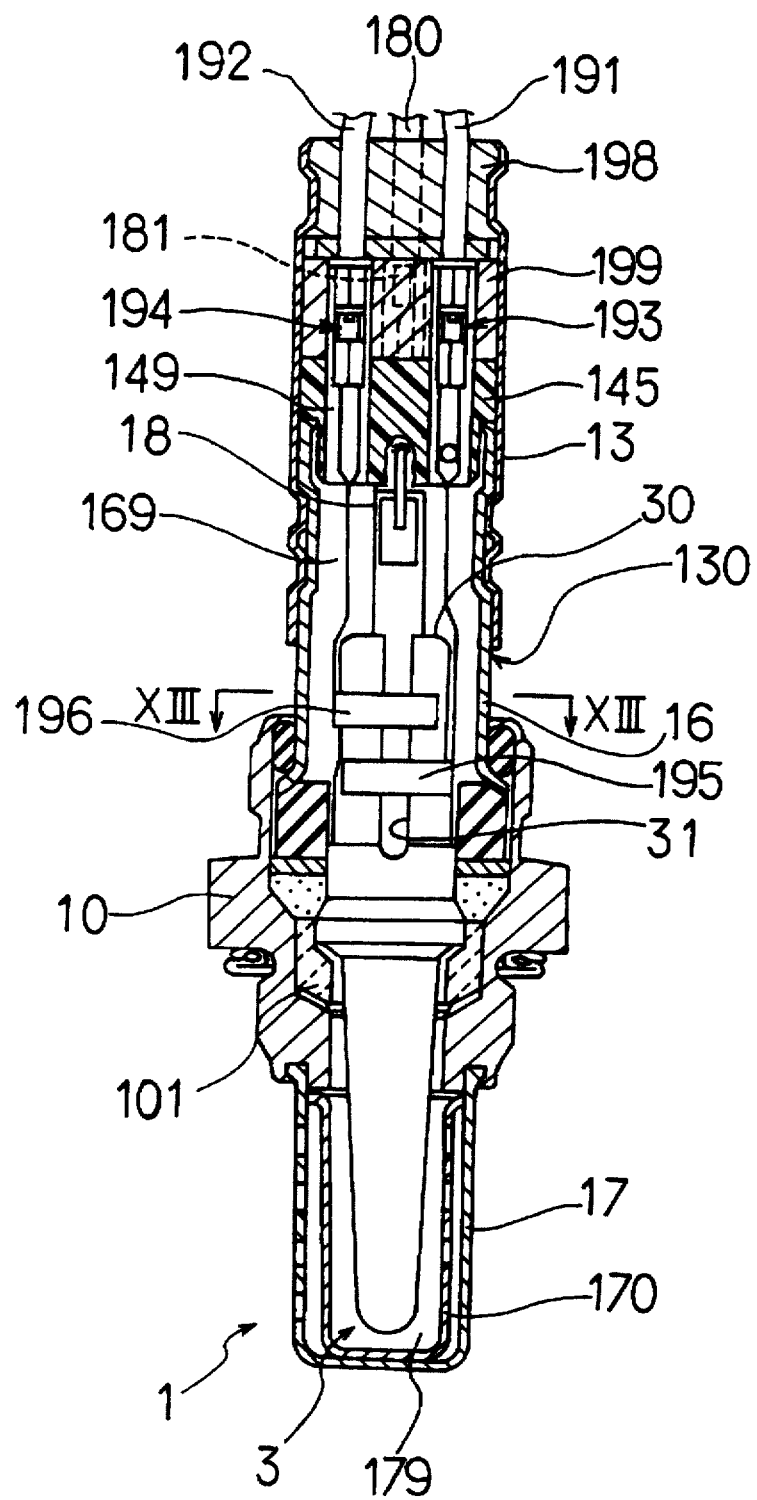
FIG. 12 is a cross sectional view illustrating a cross section of the oxygen concentration detector according to another embodiment of the present invention.
Figure 13:
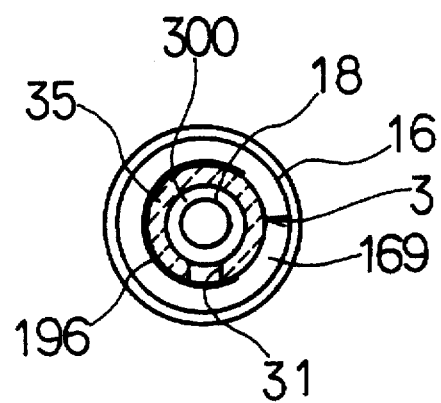
FIG. 13 is a view taken along line XIII—XIII in FIG. 12.
Figure 15:
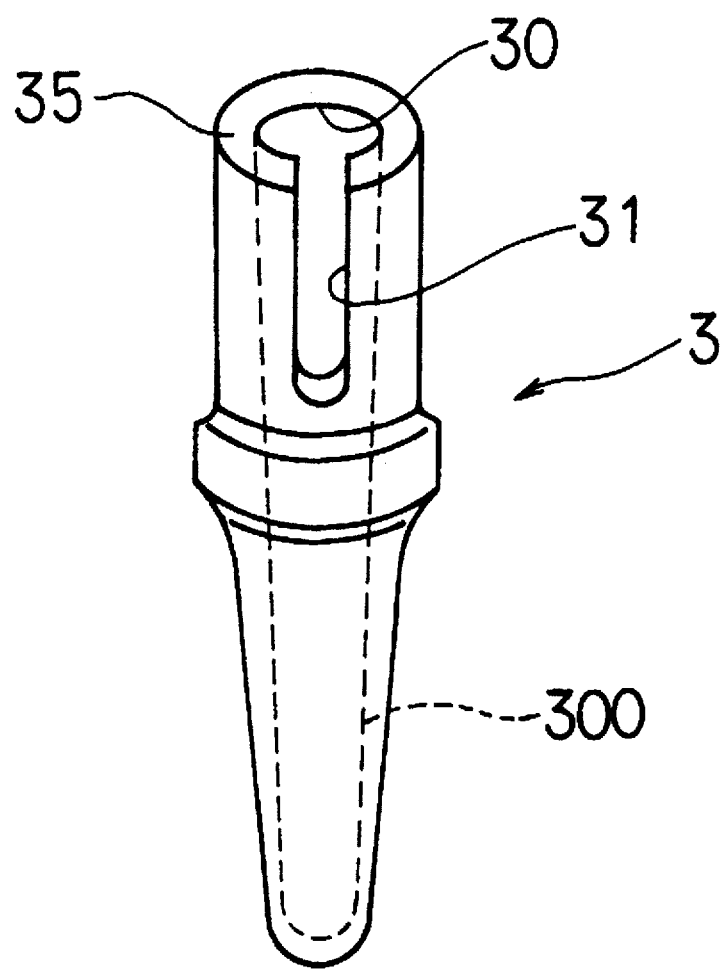
FIG. 15 is a perspective view illustrating the detecting element according to the another embodiment.

As illustrated in FIGS. 12, 13 and 15, an oxygen concentration detector 1 of this embodiment includes a housing 10, a detecting element 3 inserted into the housing 10, and covers 13 and 16 for covering a top portion of the detecting element 3 at a top portion of the housing 10. The detecting element 3 includes the atmospheric chamber 300 therein and is made of the solid electrolyte 35.

An air vent portion 130 for introducing air to the atmospheric chamber 300 of the detecting element 3 is provided between the covers 13 and 16.

Figure 14:
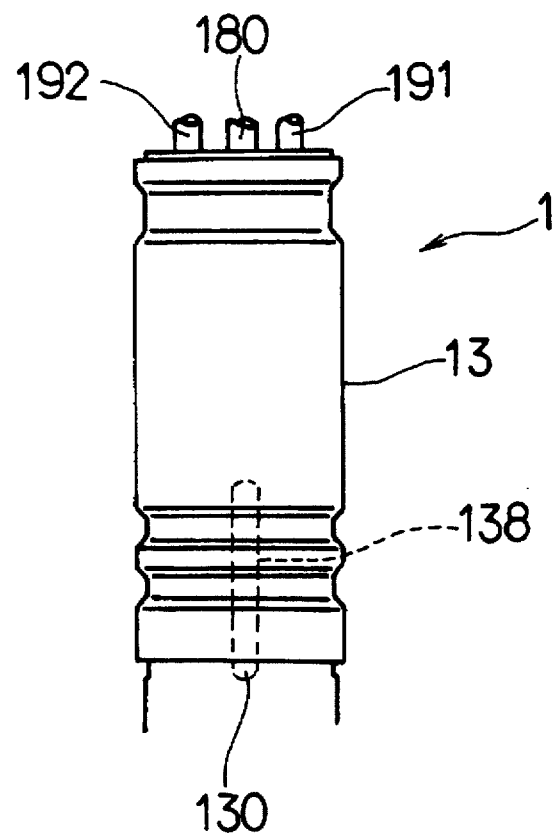
FIG. 14 is a side view illustrating a top portion of the oxygen concentration detector according to the another embodiment.

A bottom end of the cover 16 is fixed to the housing 10. As illustrated in FIG. 14, the cover 13 is provided on the cover 16 and the air vent portion 130 and an air path 138 are provided between the covers 13 and 16.

A block-shaped water repellent filter 145 is provided inside the cover 13 and at a top end of the cover 16. Bushes 198 and 199 are provided on the water repellent filter 145.

As illustrated in FIGS. 12 and 13, the space portion 169 is formed at a side portion of the air introducing path 31 of the detecting element 3 by the cover 16.

Lead terminals 193 and 194 are connected to the lead wires 191 and 192 to take out outputs of the detecting element 3, respectively. The lead terminal 181 is connected to the lead wire 180 for supplying electric current to the heater 18. An inserting portion 149 for inserting the lead terminals 193, 194 and 181 is formed inside the water repellent filter 145.

As illustrated in FIG. 15, the detecting element 3 includes an outside electrode at an outside surface of the generally the test-tube-shaped solid electrolyte 35 and an inside electrode at an inside surface facing the atmospheric chamber. The long opening hole air introducing path 31 is provided at a side surface of the solid electrolyte 35. The outside electrode is conducted to the lead terminal 193 through the connecting piece 195. The inside electrode is conducted to the lead terminal 194 through the connecting piece 196.

Figure 16:
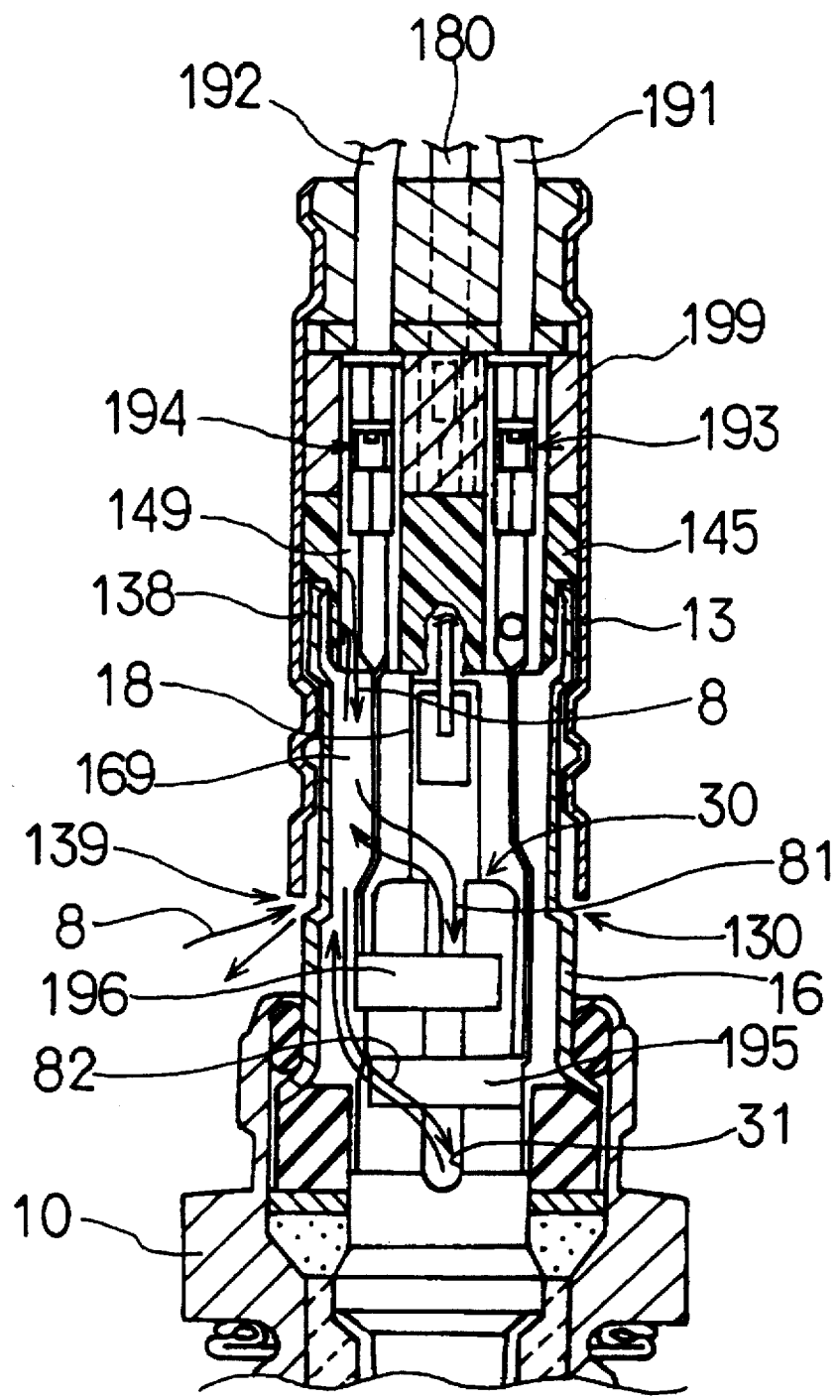
FIG. 16 is an explanatory view illustrating the air flow inside the oxygen concentration detector according to the another embodiment.

Next, flow of the air in the oxygen concentration detector 1 is described with respect to FIG. 16. The air 8 flows into the inserting portion 149 and the space portion 169 from the air vent portion 130 (in FIG. 14) through the air path 138 and an inside of the porous water repellent filter 145. The air 8 is separated into the air 81 flowing in the atmospheric chamber 300 from the top end opening portion 30 of the detecting element 3 and the air 82 flowing into the atmospheric chamber 300 from the air introducing path 31.

The other operation of the embodiment is the same as the former embodiment.

In the oxygen concentration detector 1 of this embodiment, it is possible to introduce the air to the atmospheric chamber 300 of the detecting element 3 accurately without changing a structure of the conventional oxygen concentration detector.

The other effects of the embodiment is the same as the former embodiment.

Figure 17:
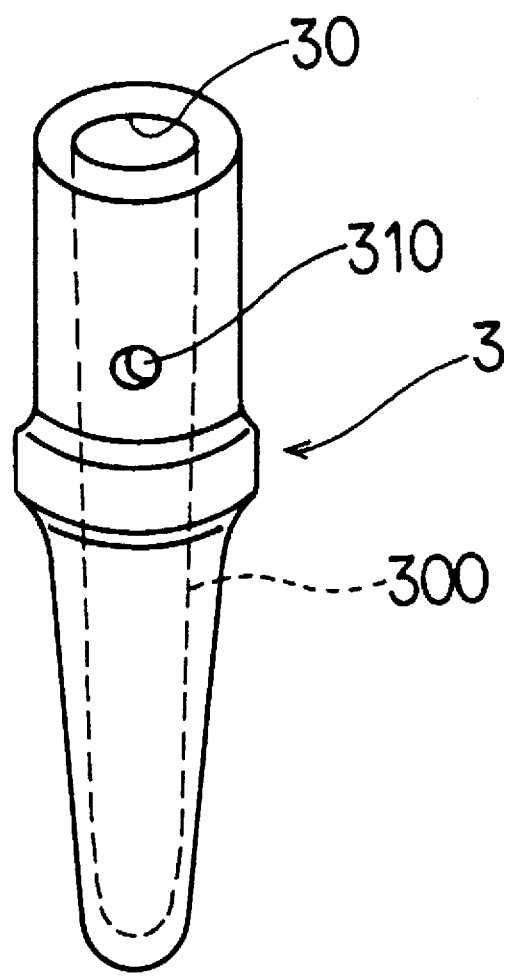
FIG. 17 is a perspective view illustrating a detecting element according to a modification of the another embodiment.
Figure 18:
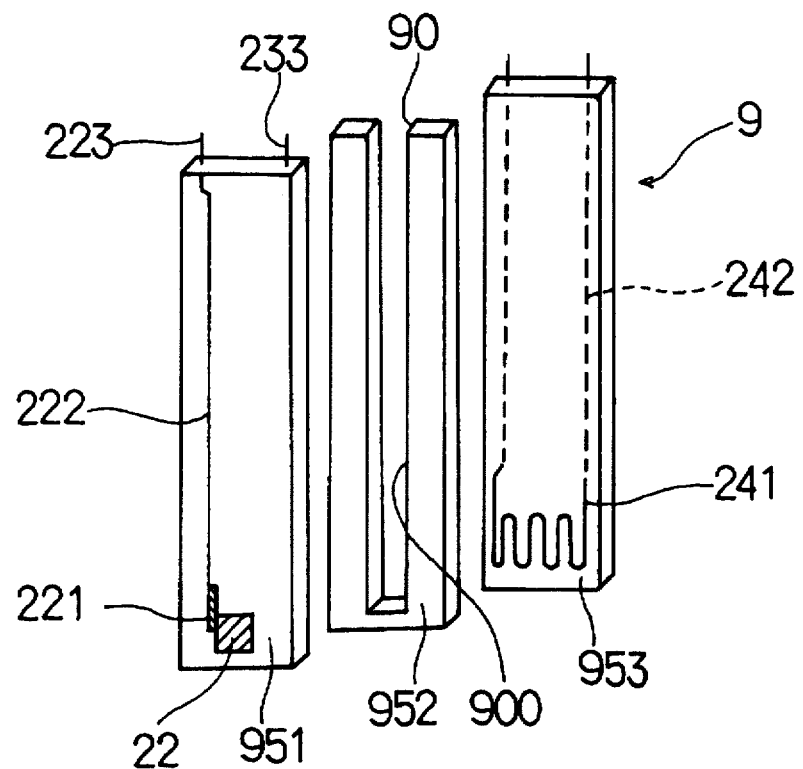
FIG. 18 is an exploded view illustrating a detecting element in prior art.
Figure 19:
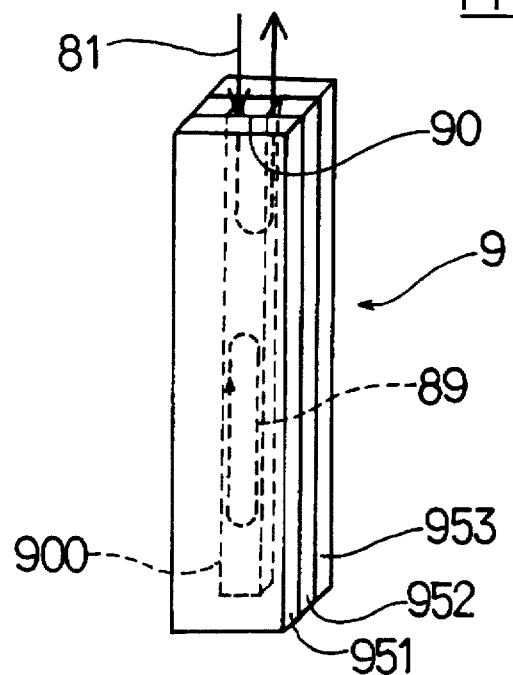
FIG. 19 is an explanatory view illustrating air flow inside the detecting element in prior art.
Figure 20:
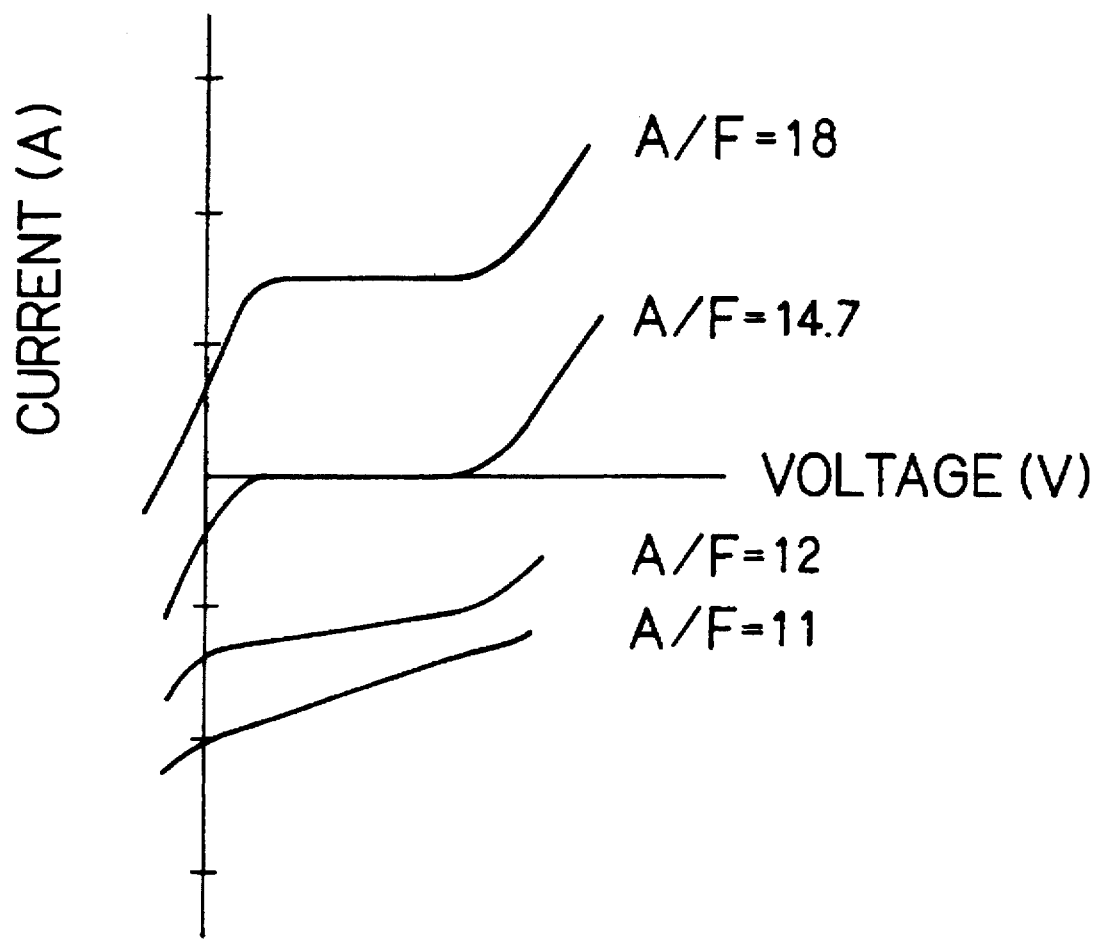
FIG. 20 is a graph illustrating an electric current and voltage characteristic for every air fuel ratio according to an air fuel ratio sensor in prior art.

The test tube type detecting element 3 illustrated in FIG. 17 includes a through hole on the solid electrolyte 35 to form the air introducing path 310.

In this case, the same operation and effect as described above can be obtained.

The present invention having been described should not be limited to the disclosed embodiments, but it may be modified in many other ways without departing from the scope and the spirit of the invention. Such changes and modifications are to be understood as being included with the scope of the present invention as defined by the appended claims.

What is claimed is:

1. An oxygen concentration detector comprising:
    a housing;
    a detecting element for detecting an oxygen concentration, at least a part of which is made of solid electrolyte, inserted into said housing with a sealing material, one end of said detecting element protruding from said housing and being enclosed such that an outer surface thereof is exposed to a measured gas to be measured, said detecting element further having a reference gas introduction chamber therein extending to the other end thereof which protrudes from said housing, and an opening portion formed at the other end so as to communicate with said reference gas introduction chamber, a reference gas being introduced into said reference gas introduction chamber through said opening portion, said measured gas and said reference gas being air tightly separated by said sealing material;
    a measured gas electrode formed on a surface of said solid electrolyte, exposed to said measured gas; and
    a reference electrode formed on a surface of said solid electrolyte facing said reference gas introduction chamber, wherein,
    said detecting element includes a side opening portion formed on a side wall thereof between the said sealing material and the other end of said detecting element so as to communicate with said reference gas introduction chamber.

2. An oxygen concentration detector according to claim 1, wherein said side opening portion is a long hole in an axial direction of said detecting element.

3. An oxygen concentration detector according to claim 1, wherein said side opening portion is formed by at least one hole.

4. An oxygen concentration detector according to claim 1, wherein said detecting element has an inclined surface in said axial direction, and a long hole is provided on said inclined surface to form said side opening portion.

5. An oxygen concentration detector according to claim 1, wherein said detecting element includes a test-tube shaped solid electrolyte.

6. An oxygen concentration detector according to claim 5, wherein said side opening portion is provided on a side wall of said test-tube shaped solid electrolyte.

7. An oxygen concentration detector according to claim 6, wherein said side opening portion is a slit.

8. An oxygen concentration detector according to claim 6, wherein said side opening portion is a hole.

9. An oxygen concentration detector according to claim 1, wherein said solid electrolyte is plate-shaped.

10. An oxygen concentration detector according to claim 9, wherein said solid electrolyte includes a slit for forming said reference gas introduction chamber.

11. An oxygen concentration detector comprising:
    a plate-shaped solid electrolyte element having one end on which a measured gas electrode and a reference electrode are formed exposed to a measured gas to be measured and an other end exposed to a reference gas;
    a plate-shaped ceramic member laminated on said solid electrolyte at a side where said reference electrode is formed, said ceramic member having an opening portion formed in an end face of said solid electrolyte element at the other end, for introducing a reference gas, said ceramic member further having a slit forming a reference gas introduction path for introducing the reference gas through said opening portion to said reference electrode;
    a housing for fixedly receiving a laminated body of said solid electrolyte element and said ceramic member; wherein,
    at least one of said solid electrolyte element and said ceramic member includes a side opening portion formed on a side wall thereof so as to communicate with said reference gas introduction path.

12. An oxygen concentration detector according to claim 11, wherein at least one of said solid electrolyte element and said ceramic member includes at the other end a slit communicating with said reference gas introduction path.

13. An oxygen concentration detector according to claim 11, wherein at least one of said solid electrolyte element and said ceramic member includes at the other end a hole communicating with said reference gas introduction path.

14. An oxygen concentration detector according to claim 11, wherein said solid electrolyte element and said ceramic member form an inclined surface at the other end.

15. An oxygen concentration detector according to claim 11, further comprising:
    a sealing material for air tightly separating the measured gas and the reference gas.

* * * * *